(12) United States Patent
Cummins (10) Patent No.: US 8,535,354 B2
(45) Date of Patent: Sep. 17, 2013

(54) BONE PLATE SYSTEM AND METHODS OF USING THE SAME

(75) Inventor: John Franklin Cummins, Kosciusko, MS (US)

(73) Assignee: Spinal USA, Inc., Parsippany, NJ (US)

( * ) Notice: Subject to any disclaimer, the term of this patent is extended or adjusted under 35 U.S.C. 154(b) by 398 days.

(21) Appl. No.: 12/842,517

(22) Filed: Jul. 23, 2010

(65) Prior Publication Data

US 2011/0022096 A1 Jan. 27, 2011

Related U.S. Application Data (60) Provisional application No. 61/228,521, filed on Jul. 24, 2009.

(51) Int. Cl.
*A61B 17/80* (2006.01)

(52) U.S. Cl.
USPC .......... 606/280; 606/286; 606/289; 606/290; 606/70; 606/71; 411/398

(58) Field of Classification Search
USPC ............ 606/70, 71, 280–299, 300, 301, 305, 606/306; 411/398, 273; 280/86.753
See application file for complete search history.

(56) References Cited

U.S. PATENT DOCUMENTS

| | | | |
|---|---|---|---|
| 4,488,543 A | 12/1984 | Tornier | |
| 5,053,036 A | 10/1991 | Perren et al. | |
| 5,067,956 A | 11/1991 | Buford, III et al. | |
| 5,151,103 A | 9/1992 | Tepic et al. | |
| 5,364,399 A | 11/1994 | Lowery et al. | |
| 5,487,743 A | 1/1996 | Laurain et al. | |
| 5,487,783 A | 1/1996 | Agnello et al. | |
| 5,549,612 A | 8/1996 | Yapp et al. | |
| 5,578,034 A | 11/1996 | Estes | |
| 5,616,144 A | 4/1997 | Yapp et al. | |
| 5,931,838 A | 8/1999 | Vito | |
| 5,951,558 A | 9/1999 | Fiz | |
| 6,139,550 A | 10/2000 | Michelson | |
| 6,152,927 A | 11/2000 | Farris et al. | |

(Continued)

OTHER PUBLICATIONS

International Search Report and Written Opinion for co-pending International Application No. PCT/US2010/043116 mailed Feb. 28, 2011 in 12 pages.

(Continued)

*Primary Examiner* — Todd Manahan
*Assistant Examiner* — Jessica Weiss
(74) *Attorney, Agent, or Firm* — Knobbe Martens Olson & Bear LLP (57) ABSTRACT

A bone plate locking system including a threaded screw body having a proximal end and a distal end and a plate with a through-hole. The proximal end includes a head. The head includes an upper portion, a groove adjacent the upper portion and a lower portion adjacent the groove, wherein a center-axis of the groove is off-axis to a center-axis of the threaded screw body. A locking ring configured to reside within the groove of the head. The through-hole includes an upper portion, a groove adjacent the upper portion and a lower portion adjacent the groove. The head is receivable in the through-hole. The locking ring is rotatably positioned around the groove of the head such that in an unlocked position the locking ring is outside the groove of the through-hole and in a locked position the locking ring is at least partially within the groove of the through-hole.

27 Claims, 11 Drawing Sheets

(56) References Cited

U.S. PATENT DOCUMENTS

| | | | |
|---|---|---|---|
| 6,171,342 B1* | 1/2001 | O'Neil et al. | 623/20.15 |
| 6,224,602 B1 | 5/2001 | Hayes | |
| 6,235,034 B1 | 5/2001 | Bray | |
| 6,258,089 B1 | 7/2001 | Campbell et al. | |
| 6,261,291 B1 | 7/2001 | Talaber et al. | |
| 6,293,949 B1 | 9/2001 | Justis et al. | |
| 6,306,139 B1 | 10/2001 | Fuentes | |
| 6,331,179 B1 | 12/2001 | Freid et al. | |
| 6,361,537 B1 | 3/2002 | Anderson | |
| 6,398,783 B1 | 6/2002 | Michelson | |
| 6,428,542 B1 | 8/2002 | Michelson | |
| 6,454,769 B2 | 9/2002 | Wagner et al. | |
| 6,503,250 B2 | 1/2003 | Paul | |
| 6,527,776 B1 | 3/2003 | Michelson | |
| 6,533,786 B1 | 3/2003 | Needham et al. | |
| 6,592,586 B1 | 7/2003 | Michelson | |
| 6,599,290 B2 | 7/2003 | Bailey et al. | |
| 6,602,255 B1 | 8/2003 | Campbell et al. | |
| 6,602,256 B1 | 8/2003 | Hayes | |
| 6,626,907 B2 | 9/2003 | Blain et al. | |
| 6,652,525 B1 | 11/2003 | Assaker et al. | |
| 6,669,700 B1 | 12/2003 | Farris et al. | |
| 6,692,503 B2 | 2/2004 | Foley et al. | |
| 6,695,846 B2 | 2/2004 | Richelsoph et al. | |
| 6,712,818 B1 | 3/2004 | Michelson | |
| 6,755,833 B1 | 6/2004 | Paul et al. | |
| 6,761,719 B2 | 7/2004 | Justis et al. | |
| 6,793,658 B2 | 9/2004 | LeHuec | |
| 6,890,335 B2 | 5/2005 | Grabowski et al. | |
| 6,916,320 B2 | 7/2005 | Michelson | |
| 6,926,718 B1 | 8/2005 | Michelson | |
| 6,936,050 B2 | 8/2005 | Michelson | |
| 6,936,051 B2 | 8/2005 | Michelson | |
| 6,945,973 B2 | 9/2005 | Bray | |
| 6,945,975 B2 | 9/2005 | Dalton | |
| 6,969,390 B2 | 11/2005 | Michelson | |
| 6,979,334 B2 | 12/2005 | Dalton | |
| 6,989,012 B2 | 1/2006 | LeHuec et al. | |
| 7,001,387 B2 | 2/2006 | Farris et al. | |
| 7,001,389 B1 | 2/2006 | Navarro et al. | |
| 7,004,944 B2 | 2/2006 | Gause | |
| 7,011,665 B2 | 3/2006 | Null et al. | |
| 7,041,105 B2 | 5/2006 | Michelson | |
| 7,044,952 B2 | 5/2006 | Michelson | |
| 7,048,739 B2 | 5/2006 | Konieczynski et al. | |
| 7,060,067 B2 | 6/2006 | Needham et al. | |
| 7,074,221 B2 | 7/2006 | Michelson | |
| 7,077,844 B2 | 7/2006 | Michelson | |
| 7,097,645 B2 | 8/2006 | Michelson | |
| 7,118,573 B2 | 10/2006 | Michelson | |
| 7,169,150 B2 | 1/2007 | Shipp et al. | |
| 7,172,627 B2 | 2/2007 | Fiere et al. | |
| 7,210,884 B2 | 5/2007 | Shindoh | |
| 7,273,481 B2* | 9/2007 | Lombardo et al. | 606/86 A |
| 7,288,094 B2 | 10/2007 | Lindemann et al. | |
| 7,288,095 B2 | 10/2007 | Baynham et al. | |
| 7,306,605 B2 | 12/2007 | Ross | |
| 7,309,340 B2 | 12/2007 | Fallin et al. | |
| 7,438,715 B2 | 10/2008 | Doubler et al. | |
| 7,452,370 B2 | 11/2008 | Anderson | |
| 7,625,381 B2 | 12/2009 | Michelson | |
| 7,651,497 B2 | 1/2010 | Michelson | |
| 7,704,255 B2 | 4/2010 | Michelson | |
| 2003/0187440 A1 | 10/2003 | Richelsoph et al. | |
| 2004/0087951 A1 | 5/2004 | Khalili | |
| 2004/0097935 A1 | 5/2004 | Richelsoph et al. | |
| 2004/0127900 A1 | 7/2004 | Konieczynski et al. | |
| 2004/0153069 A1 | 8/2004 | Paul | |
| 2004/0220566 A1 | 11/2004 | Bray | |
| 2004/0220571 A1 | 11/2004 | Assaker et al. | |
| 2004/0236334 A1 | 11/2004 | Michelson | |
| 2005/0010227 A1 | 1/2005 | Paul | |
| 2005/0021032 A1 | 1/2005 | Koo | |
| 2005/0075633 A1 | 4/2005 | Ross | |
| 2005/0131412 A1 | 6/2005 | Olevsky et al. | |
| 2005/0187551 A1 | 8/2005 | Orbay et al. | |
| 2005/0187553 A1 | 8/2005 | Grabowski et al. | |
| 2005/0228386 A1 | 10/2005 | Ziolo et al. | |
| 2005/0251138 A1 | 11/2005 | Boris et al. | |
| 2005/0261390 A1 | 11/2005 | Frances et al. | |
| 2005/0261689 A1 | 11/2005 | Lin | |
| 2005/0283152 A1 | 12/2005 | Lindemann et al. | |
| 2006/0009770 A1 | 1/2006 | Speirs et al. | |
| 2006/0064097 A1 | 3/2006 | Bray | |
| 2006/0085001 A1 | 4/2006 | Michelson | |
| 2006/0100626 A1 | 5/2006 | Rathbun et al. | |
| 2006/0106387 A1 | 5/2006 | Fanger et al. | |
| 2006/0122603 A1 | 6/2006 | Kolb | |
| 2006/0122604 A1 | 6/2006 | Gorhan et al. | |
| 2006/0122605 A1 | 6/2006 | Suh et al. | |
| 2006/0149241 A1 | 7/2006 | Richelsoph et al. | |
| 2006/0149256 A1 | 7/2006 | Wagner et al. | |
| 2006/0155285 A1 | 7/2006 | Anderson | |
| 2006/0161157 A1 | 7/2006 | Mosca et al. | |
| 2006/0276793 A1 | 12/2006 | Berry | |
| 2006/0293668 A1 | 12/2006 | May et al. | |
| 2007/0043366 A1 | 2/2007 | Pfefferle et al. | |
| 2007/0073297 A1 | 3/2007 | Reynolds | |
| 2007/0123879 A1 | 5/2007 | Songer et al. | |
| 2007/0123884 A1 | 5/2007 | Abdou | |
| 2007/0162013 A1 | 7/2007 | Jacene et al. | |
| 2007/0162019 A1 | 7/2007 | Burns et al. | |
| 2007/0213728 A1 | 9/2007 | Lindemann et al. | |
| 2007/0225718 A1 | 9/2007 | Ensign | |
| 2007/0239163 A1 | 10/2007 | Strnad et al. | |
| 2008/0009870 A1 | 1/2008 | Lombardo et al. | |
| 2008/0015592 A1 | 1/2008 | Long et al. | |
| 2008/0021477 A1 | 1/2008 | Strnad et al. | |
| 2008/0033437 A1 | 2/2008 | Shipp et al. | |
| 2008/0097443 A1 | 4/2008 | Campbell | |
| 2008/0097444 A1 | 4/2008 | Erickson et al. | |
| 2008/0114359 A1 | 5/2008 | Murner et al. | |
| 2008/0161862 A1 | 7/2008 | Ensign | |
| 2008/0172092 A1 | 7/2008 | Kraemer | |
| 2008/0177330 A1 | 7/2008 | Ralph et al. | |
| 2008/0234748 A1 | 9/2008 | Wallenstein et al. | |
| 2008/0243192 A1 | 10/2008 | Jacene et al. | |
| 2008/0269807 A1 | 10/2008 | Simon et al. | |
| 2008/0287999 A1 | 11/2008 | Markworth | |
| 2009/0062863 A1 | 3/2009 | Peppers | |

OTHER PUBLICATIONS

U.S. Appl. No. 12/842,901, filed Jul. 23, 2010, Walker et al.
International Preliminary Report on Patentability for related PCT Application No. PCT/US2010/043116, issued on Jan. 24, 2012, in 5 pages.

* cited by examiner

BONE PLATE SYSTEM AND METHODS OF USING THE SAME

CROSS-REFERENCE TO RELATED APPLICATIONS

This application claims the priority benefit of U.S. Provisional Application Ser. No. 61/228,521, filed on Jul. 24, 2009, the entirety of which is hereby incorporated by reference.

BACKGROUND

1. Field of the Invention

Disclosed herein are bone plate systems related to the field of orthopedic surgery. More particularly, certain embodiments disclosed herein relate to bone plate systems with a locking screw and an anterior cervical spinal plate and methods of use.

2. Description of the Related Art

Spinal fusion encompasses a surgical technique in which two or more vertebrae are connected together. This technique may be used for multiple indications, including abnormal spinal curvature (e.g., scoliosis) and weakening or injuring of the vertebrae or spinal disc.

In some instances, this process is accomplished and/or supplemented using a plate to join together adjacent vertebrae. The plate is affixed by implanting a plurality of screws through the plate and into the vertebrae bodies of adjacent vertebrae. A screw may have an enlarged head that interfaces with the plate having a corresponding cavity, thus allowing for a range of polyaxial articulation between the screw and the plate. A common risk with prior bone plate system designs include backing out and loosening of the screw after being implanted.

SUMMARY

Described herein are bone plate locking systems that can include a screw, a locking ring and a plate. Methods of assembling and implanting the bone plate locking systems described herein are also included. These bone plate locking systems and related methods are described in greater detail below.

In certain embodiments, the bone plate locking system includes a threaded screw body having a proximal end and a distal end. The proximal end includes a head. The head includes an upper portion, a groove adjacent the upper portion and a lower portion adjacent the groove. In addition, a center-axis of the groove is off-axis to a center-axis of the threaded screw body. The bone plate system further includes a locking ring that is configured to reside within the groove of the head, and a plate that includes an anterior surface, a posterior surface and a through-hole through the anterior surface and the posterior surface. The through-hole includes an upper portion, a groove adjacent the upper portion and a lower portion adjacent the groove. The head is receivable in the through-hole. The locking ring is rotatably positioned around the groove of the head such that in an unlocked position the locking ring is outside the groove of the through-hole and in a locked position the locking ring is at least partially within the groove of the through-hole.

In some embodiments, the groove of the head defines an at least partially circular surface. The locking ring further includes an outer curved surface, an inner curved surface, an anterior surface and a posterior surface. In certain embodiments, the bone plate locking system includes a notch in at least a portion of the upper portion of the head. The locking ring further includes a first protrusion on at least a portion of the posterior surface of the locking ring that is configured to reside within the notch in the upper portion of the head. The locking ring is rotatably positioned around the groove of the head such that in an unlocked position the first protrusion is at one end of the notch in the upper portion of the head, and in a locked position the first protrusion is at another end of the notch in the upper portion of the head.

In certain embodiments, the bone plate locking system includes a notch in at least a portion of the groove of the head, and the locking ring further includes a second protrusion on at least a portion of the inner surface. The locking ring being rotatably positioned around the groove of the head such that in an unlocked position the second protrusion of the locking ring is within the notch in the groove of the head, and in a locked position the second protrusion of the locking ring is outside the notch in the groove of the head.

In certain embodiments, a method of fixing adjacent vertebrae includes providing a plate that includes an anterior surface, a posterior surface and a plurality of through-holes through the anterior surface and the posterior surface, and positioning the plate on the anterior surface of at least two adjacent vertebral bodies. At least one through-hole is positioned over a first vertebral body and a second through-hole is positioned over a second vertebral body. The method further includes inserting a first screw through a first through-hole into the first vertebral body and a second screw through a second through-hole into the second vertebral body. The first and second screws include heads positioned within first and second through-holes and threaded bodies engaging the vertebral bodies. The method includes rotating a locking ring positioned within a groove of the head of one of said screws to a position where the locking ring is positioned at least partially within a groove of one of the through-holes to limit the screw backing out of the through-hole.

DETAILED DESCRIPTION

Figure 1:
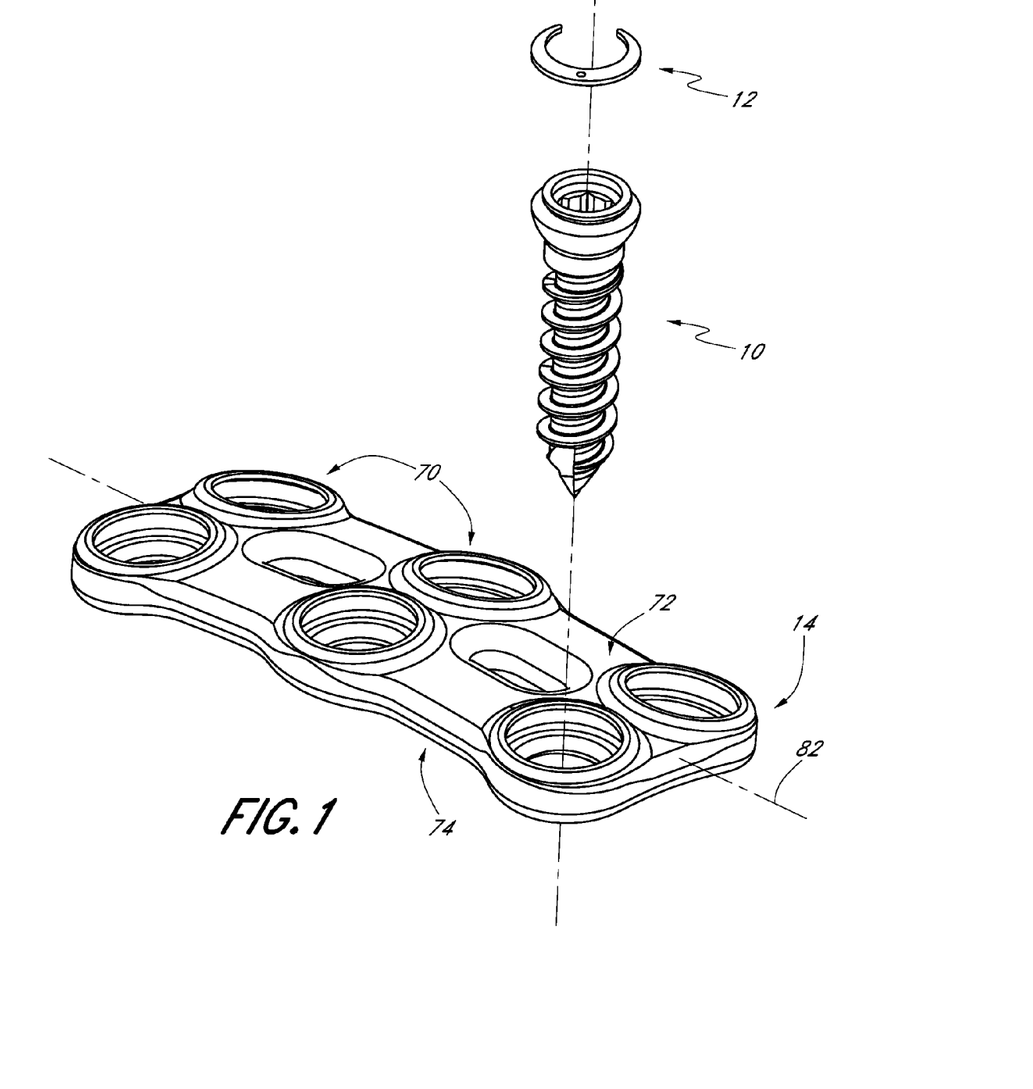
FIG. 1 is an exploded view of an embodiment of a bone plate system.

FIG. 1 shows an embodiment directed to a bone plate locking system which can include one or more screws 10, a locking ring 12 and a plate 14. In certain embodiments, the screw 10 is inserted into the plate 14 and the screw 10 is screwed into a vertebra. The locking ring 12 can be rotated between an unlocked position and a locked position so that in a locked position the screw 10 will resist backing out of the plate 14.

Figure 2:
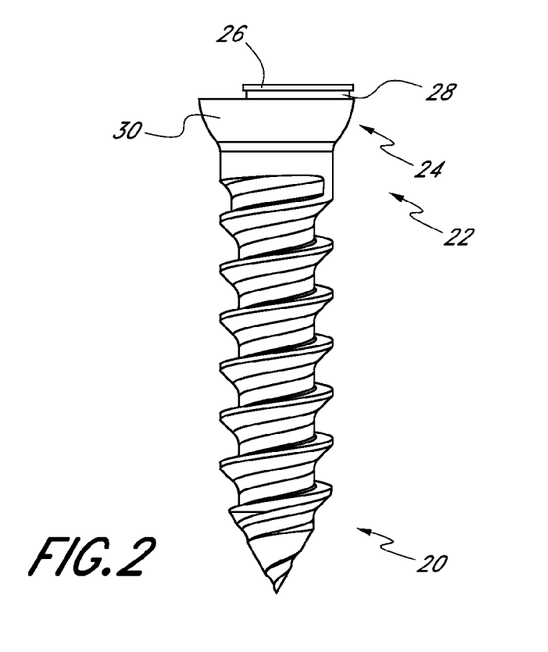
FIG. 2 is a side view of an embodiment of a screw.

FIG. 2 illustrates a side view of one embodiment of a screw 10. The screw 10 may be a threaded screw body. The screw 10 may have a proximal end 22 and a distal end 20. The distal end 20 may be at least partially threaded. In some embodiments, the distal end 20 of the screw body 10 may be adapted for implantation into the spine of a patient. For example, the distal end 20 of the screw 10 can be adapted for implantation into a vertebral body of a patient's lumber, cervical or thoracic spine. The proximal end 22 may include an enlarged head 24. The head 24 may have an upper portion 26, a groove 28 adjacent the upper portion 26, and a lower portion 30 adjacent the groove 28.

Figure 3:
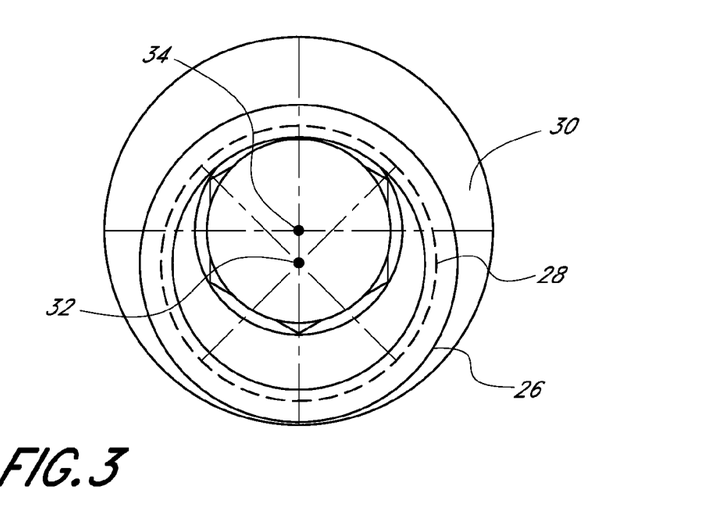
FIG. 3 is a top view of the screw illustrated in FIG. 2.

The groove 28 can define a curved surface, and preferably an at least partially circular surface. FIG. 3 illustrates a top view of the screw 10. The screw 10 can have a center of axis 34, and the groove 28 can also have a center of axis 32. The center of axis 34 of the screw 10 can be substantially parallel to the length of the screw 10 and preferably passes through the distal tip of the distal end 20 of the screw 10. The center of axis 32 of the groove 28 can be off-axis to the center of axis 34 of the screw 10. For example, the center of axis 32 of the groove 28 can be different from the center of axis 34 of the screw 10. In certain embodiments, the center of axis 32 of the groove 28 and the center of axis 34 of the screw 10 are substantially parallel. In other embodiments, the center of axis 32 of the groove 28 and the center of axis 34 of the screw 10 are non-parallel. In certain embodiments, at least a portion of the upper portion 26 and/or the lower portion 30 of the head 24 extend beyond an outer periphery of the groove 28. In further embodiments, substantially all of the upper portion 26 and/or the lower portion 30 of the head 24 extend beyond an outer periphery of the groove 28. As shown in FIG. 2, at least a portion of the lower portion 30 extends beyond an outer periphery of the upper portion 26 of the head 24. The lower portion 30 of the head 24 preferably has a planar surface on the proximal end of the lower portion 30 and is oriented substantially perpendicular to the center of axis 34 of the screw 10. The upper portion 26 of the head can also have a planar surface on the distal end of the upper portion 26 and is oriented substantially perpendicular to the center of axis 34 of the screw 10. The planar surfaces can be substantially flat. In other embodiments, other suitable screw head features can be employed to facilitate coupling the screw head with the locking ring. For example, the screw head may include one or more grooves, slots, tracks, holes, ridges, indentations, protrusions, pins, followers or other features to facilitate holding a locking ring in a preferred configuration, or facilitate moving the locking ring from a first position to a second position relative to the screw head. Various shapes and geometries of the screw head may facilitate holding or moving the locking ring in a preferred manner.

Figure 4:
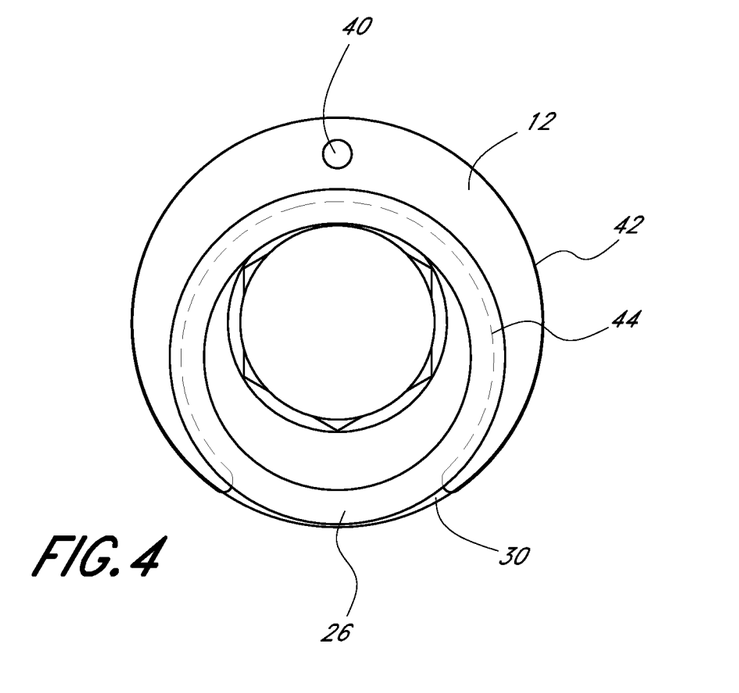
FIG. 4 is a top view of the screw illustrated in FIG. 3 and an embodiment of a locking ring in an unlocked position.
Figure 5:
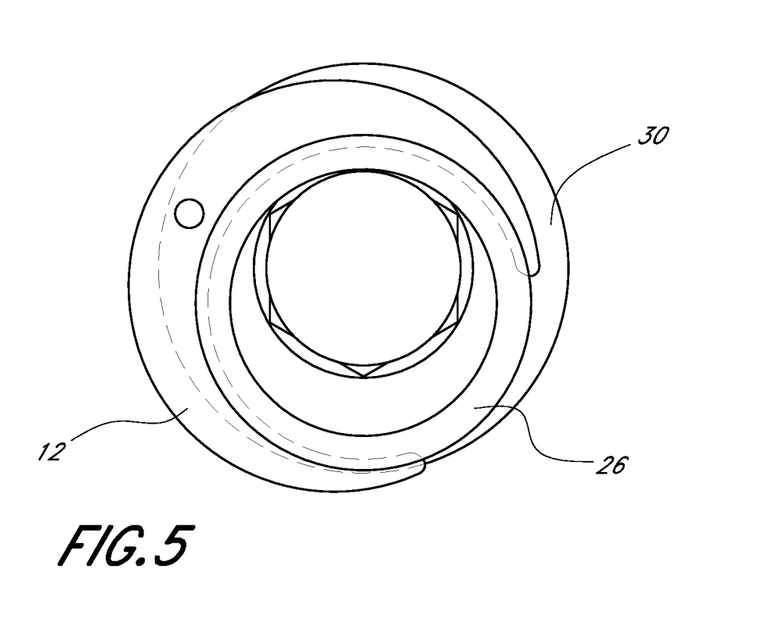
FIG. 5 is a top view of the screw illustrated in FIG. 3 and an embodiment of a locking ring in a locked position.
Figure 6:
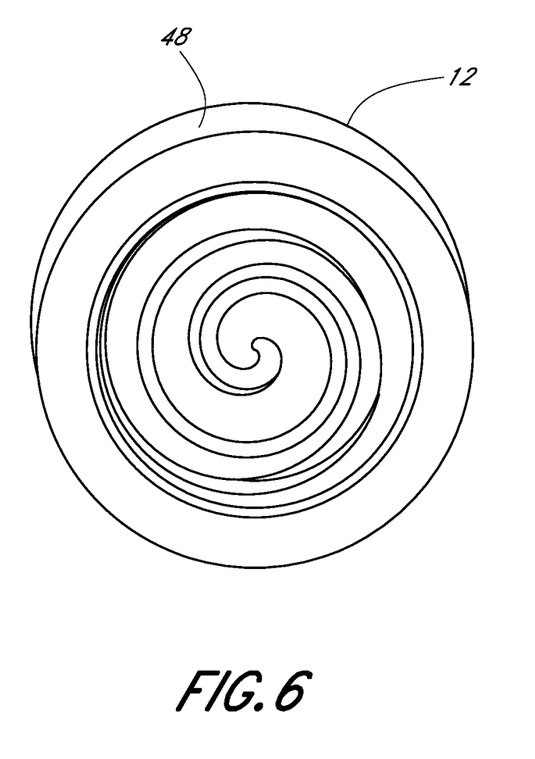
FIG. 6 is a bottom view of the screw and the locking ring in the configuration illustrated in FIG. 5.

FIGS. 4 and 5 illustrate top views of a head 24 of a screw 10 and a locking ring 12. The locking ring 12 preferably resides at least partially within the groove 28 of the head 24. In certain embodiments, the locking ring 12 is removable from the groove 28. The locking ring 12 can be at least partially rotatable within the groove 28 of the head 24. The locking ring 12 may include a means to rotate the locking ring 12. For example, the locking ring 12 may include a hole 40 so that a tool can be inserted into the hole 40 to rotate the locking ring 12. The position of the locking ring 12 in FIG. 4 illustrates an unlocked position. FIG. 5 illustrates the locking ring 12 in a locked position. The locking ring 12 rotates around the center of axis 32 of the groove 28. The locking ring 12 may be a continuous ring or may not be a continuous ring. For example, the locking ring 12 can have a c-shape, as shown in FIGS. 1, 4 and 5. The locking ring 12 may have an outer curved surface 42 and an inner curved surface 44. In certain embodiments, at least a portion of the locking ring 12 has a distance between the outer curved surface 42 and the inner curved surface 44 that is greater than at least another portion of the locking ring 12. For example, the locking ring 12 can have a partial moon shape or crescent shape. In the locked position, the locking ring 12 may at least partially extend outwardly beyond the lower portion 30 of the head 24, as illustrated in FIG. 5. FIG. 6 illustrates a bottom view of the locking ring 12 in a locked position. In certain embodiments, the locking ring 12 does not extend beyond the lower portion 30 of the head 24 in an unlocked position. In some embodiments, the locking ring 12 is able to rotate completely around the center of axis 32 of the groove 28. In other embodiments, the locking ring 12 is only able to partially rotate around the center of axis 32 of the groove 28. In other embodiments, other suitable locking ring features can be employed to facilitate coupling the screw head with the locking ring. For example, the locking may include one or more grooves, slots, tracks, holes, ridges, indentations, protrusions, pins, followers or other features to facilitate holding a locking ring in a preferred configuration, or facilitate moving the locking ring from a first position to a second position relative to the screw head. Various shapes and geometries of the locking ring may facilitate holding or moving the locking ring in a preferred manner. Additionally, locking rings can include any suitable shape adapted for coupling the locking ring to the screw head and/or adapted for movement relative to the screw head between an unlocked configuration and a locked configuration. For example, movement of locking ring relative to the screw head may include rotational movement, translational movement, pivotal movement, and/or other suitable movement. Additionally, locking rings can include any suitable shape for facilitating screw insertion in a first position and providing a blocking feature to limit screw backout in a second position. For example, the shape of the locking rings can include one or more of the following shapes: ring shaped, crescent shaped, u-shaped, v-shaped, c-shaped, j-shaped, symmetrical, non-symmetrical, elongated, oblong, curved, angled and/or any other shape suitable for not interfering with screw insertion in a first position and suitable for blocking the screw to limit back out in a second position. In some embodiments the locking rings can be movably fixed or attached to the screw head prior to insertion of the screw in a patient. In other embodiments the locking rings can be coupled to the screw head after insertion.

Figure 7:
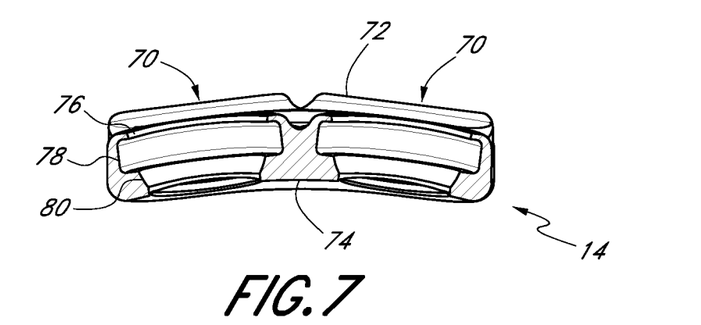
FIG. 7 is a cross-sectional view of an embodiment of a plate.

FIG. 7 illustrates a cross-sectional view through a plate 14. The plate includes a posterior surface 74, an anterior surface 72 and at least one through-hole 70 through the posterior surface 74 and the anterior surface 72. In certain embodiments, the plate 14 includes more than one through-hole 70. The through-hole 70 can include an upper portion 76, a groove 78 adjacent the upper portion 76, and a lower portion 80 adjacent the groove 78. The embodiment of FIG. 1 illustrates three pairs of openings or through-holes 70 that are configured to be aligned over adjacent vertebral bodies. The plate 14 may be placed over a desired spinal location, such as on in the lumbar, thoracic or cervical spine. For example, the plate 14 may be configured to be placed over an anterior surface of the spine, and in an embodiment, the posterior surface may be concave along a longitudinal axis 82 of the plate 14.

Figure 8:
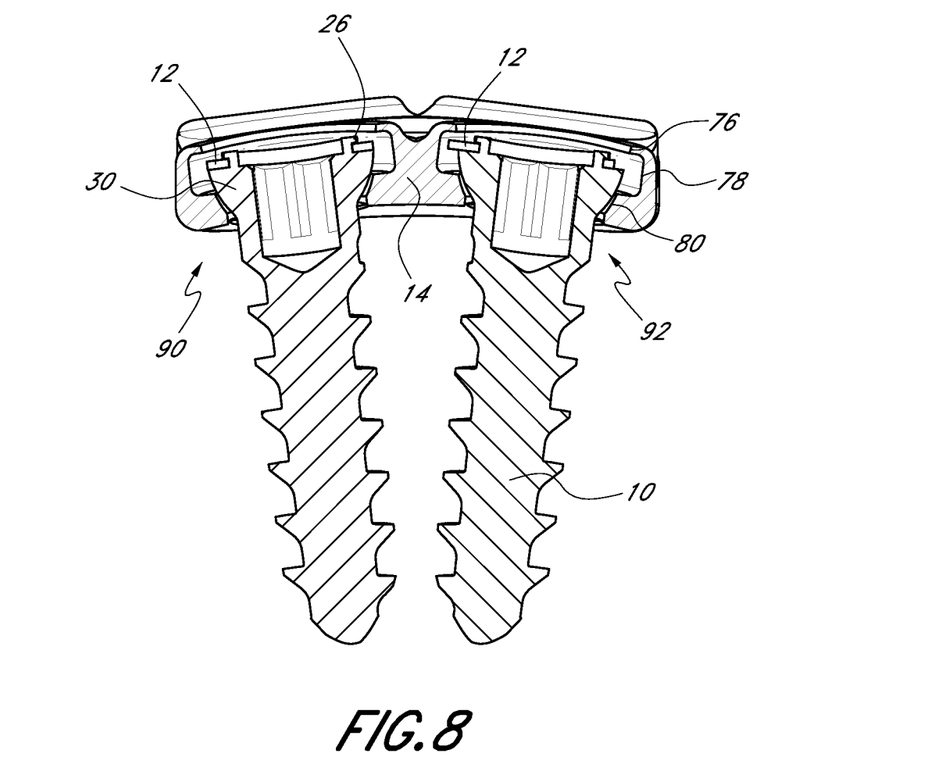
FIG. 8 is a cross-sectional view of an embodiment of a bone plate system wherein the locking ring on the left is in an unlocked position and the locking ring on the right is in a locked position.

FIG. 8 illustrates a cross-sectional view of screws 10 inserted in the through-holes 70 of a plate 14. The locking ring 12 within the screw 10 on the left 90 is in an unlocked position, while the locking ring 12 within the screw 10 on the right 92 is in a locked position. The head 24 of the screw 10 can be receivable in the through-hole 70 of the plate 14. For example, the upper portion 76 of the through-hole 70 can be large enough to allow the screw 10 to pass through when the locking ring 12 is in an unlocked position. For example, a diameter of the head 24 of the screw 10 can be smaller than a diameter of the upper portion 76 of the through-hole 70. The lower portion 80 of the through-hole 70 preferably limits the screw 10 from passing completely through the through-hole 70. For example, a diameter of the lower portion 80 of the through-hole 70 can be smaller than a diameter of the lower portion 30 of the screw 10.

In certain embodiments, the lower portion 80 of the through-hole 70 and/or the lower portion 30 of the screw 10 are curved. The lower portion 30 of the screw 10 can rest against the lower portion 80 of the through-hole 70 to press the plate 14 against the vertebrae when the screw 10 is screwed into the vertebrae. At least a portion of the upper portion 76 and/or lower portion 80 of the through-hole 70 can extend beyond the groove 78 of the through-hole 70 to form the groove 78. For example, a diameter of the upper portion 76 and/or lower portion 80 of the through-hole 70 can be smaller than a diameter of the groove 78 of the through-hole 70. In certain embodiments, a diameter of the lower portion 80 of the through-hole 70 is smaller than a diameter of the groove 78 and/or the upper portion 76 of the through-hole 70. In the unlocked position, the locking ring 12 is outside the groove 78 of the through-hole 70. In the locked position, the locking ring 12 is at least partially within the groove 78 of the through-hole 70. When the locking ring 12 is in the locked position, the locking ring 12 substantially limits the screw 10 from backing out of the through-hole 70 of the plate 14. In certain embodiments, the locking ring 12 does not touch a surface of the through-hole 70, and in other embodiments, the locking ring 12 may touch a surface of the through-hole 70. If the screw 10 at least partially backs out of the plate 14, the locking ring 12 may impinge on the upper portion 76 of the through-hole 70. By impinging on the upper portion 76 of the through-hole 70, the locking ring 12 substantially limits the screw 10 from backing out. In certain embodiments, the locking ring 12 can be rotated between the locked position and the unlocked position so as to allow the screw 10 to be removable after the screw 10 has been inserted into the plate 14.

Figure 9:
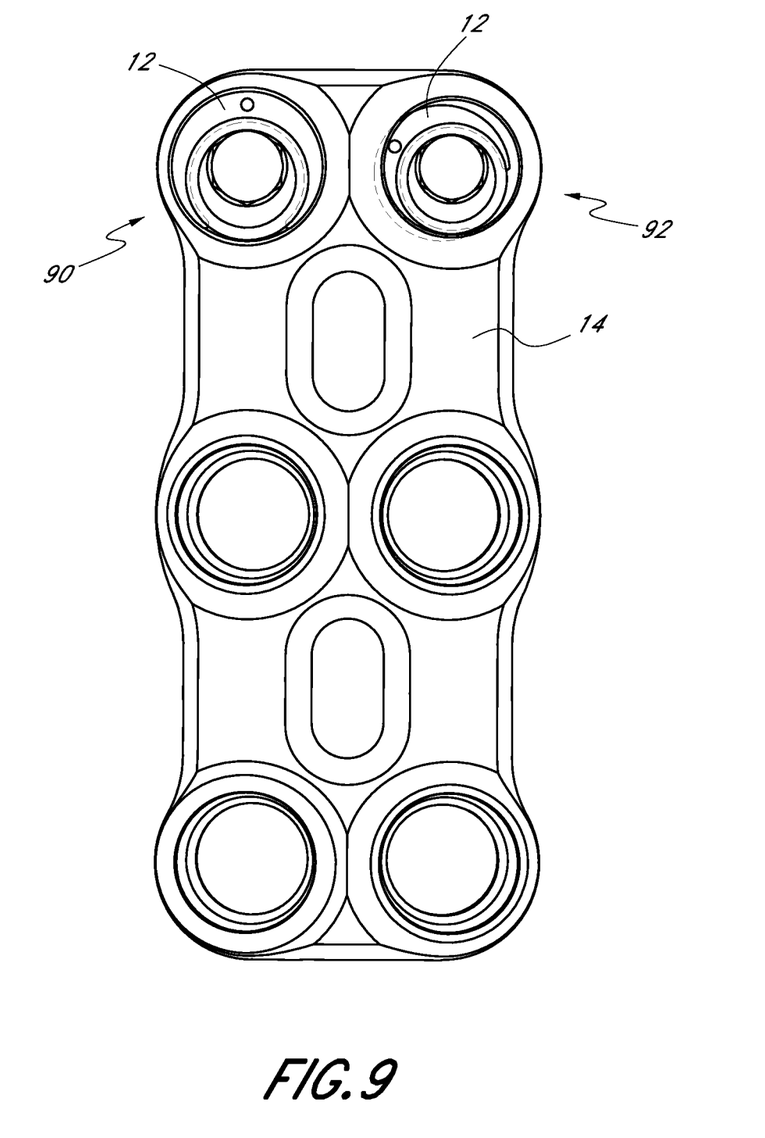
FIG. 9 is a top view of the bone plate system illustrated in FIG. 8 wherein the locking ring on the left is in an unlocked position and the locking ring on the right is in a locked position.

FIG. 9 illustrates a top view of a plate 14 with screws 10 inserted into two through-holes 70. The locking ring 12 within the screw 10 on the left 90 is in an unlocked position, while the locking ring 12 within the screw 10 on the right 92 is in a locked position. The locking ring 12 in an unlocked position is not within the groove 78 of the through-hole 70. The locking ring 12 in a locked position is at least partially within the groove 78 of the through-hole 70. The locking ring 12 in a locked position is also at least partially under the upper portion 76 of the through-hole 70. In some embodiments, the locking ring 12 is placed within the groove 78 of the screw 10 prior to the screw 10 being inserted into the through-hole 70. In other embodiments, the locking ring 12 is placed within the groove 78 of the screw 10 when the screw 10 is at least partially inserted into the through-hole 70. In even further embodiments, the locking ring 12 is placed within the groove 78 of the screw 10 after the screw 10 is fully inserted in the through-hole 70.

Figures 10, 11:
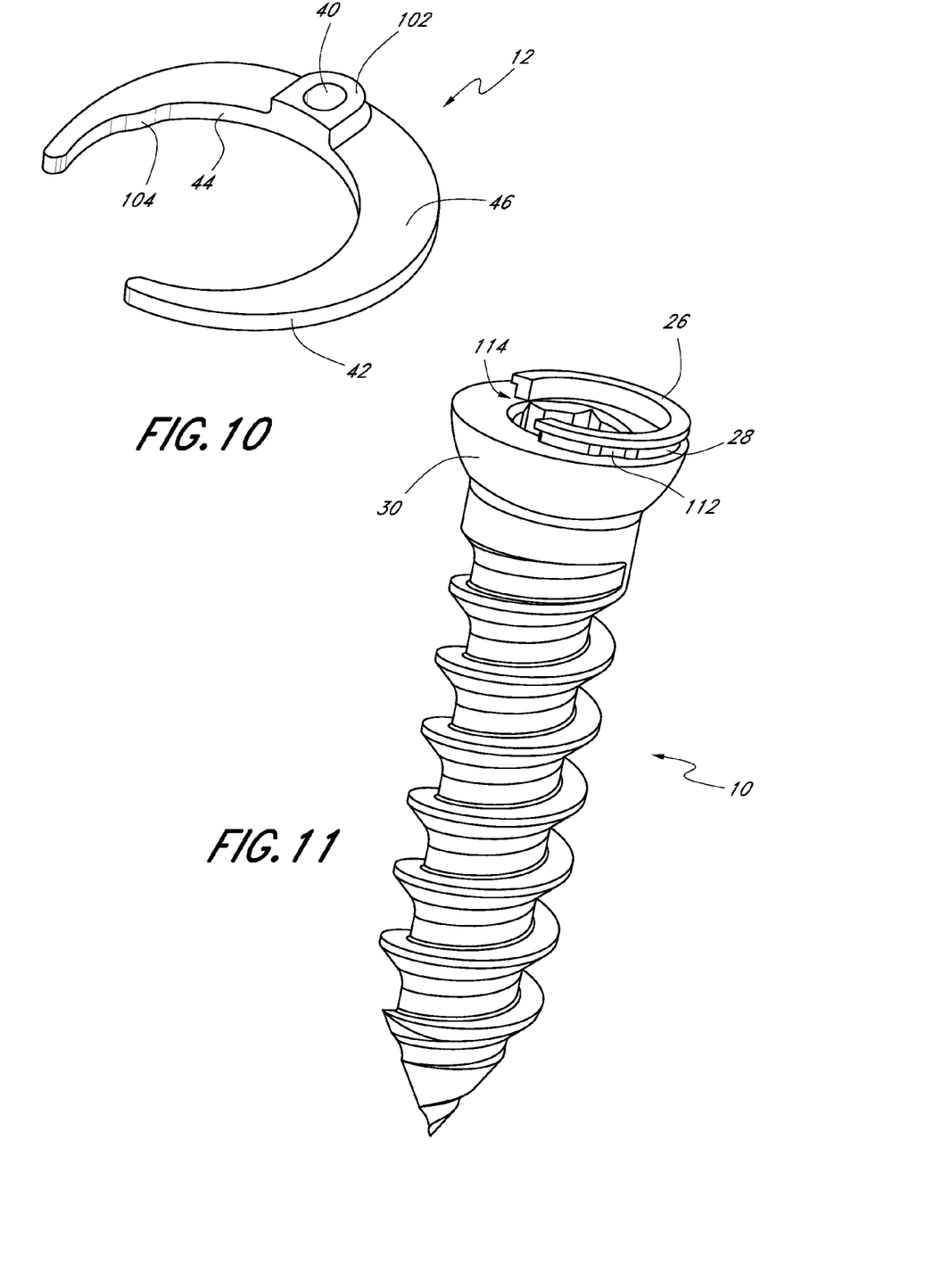
FIG. 10 is a perspective view of an embodiment of a locking ring.
FIG. 11 is a perspective view of an embodiment of a screw.
Figure 12A:
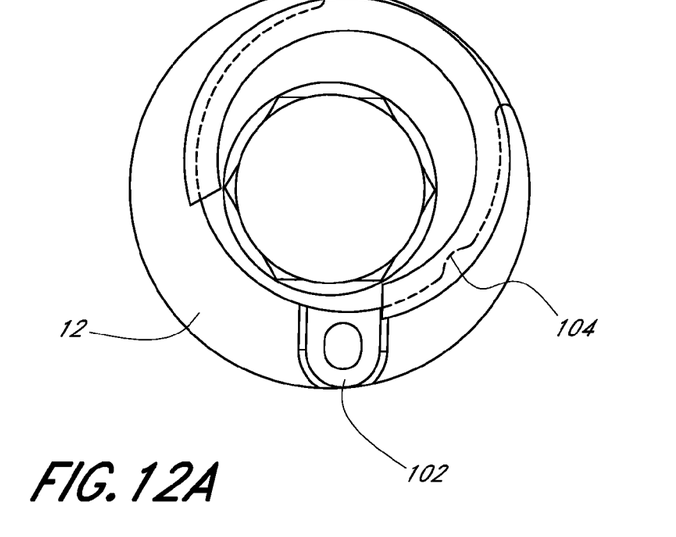
FIG. 12A is a top view of the screw illustrated in FIG. 11 and the locking ring illustrated in FIG. 10 in an unlocked position.
Figure 12B:
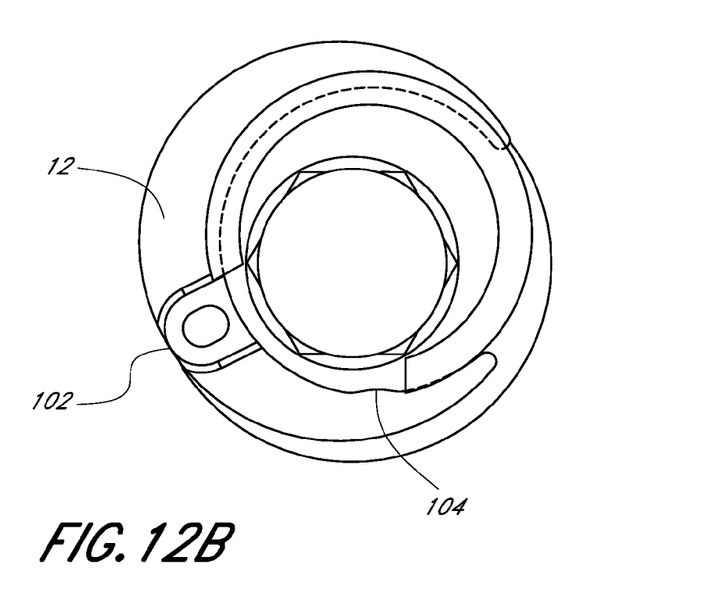
FIG. 12B is a top view of the screw illustrated in FIG. 11 and the locking ring illustrated in FIG. 10 in a locked position.
Figure 12C:
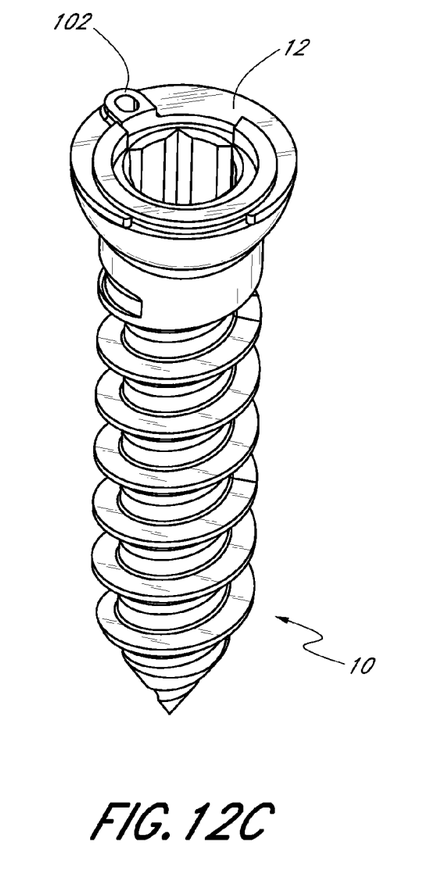
FIG. 12C is a perspective view of the screw and the locking ring illustrated in FIG. 12A in an unlocked position.
Figure 12D:
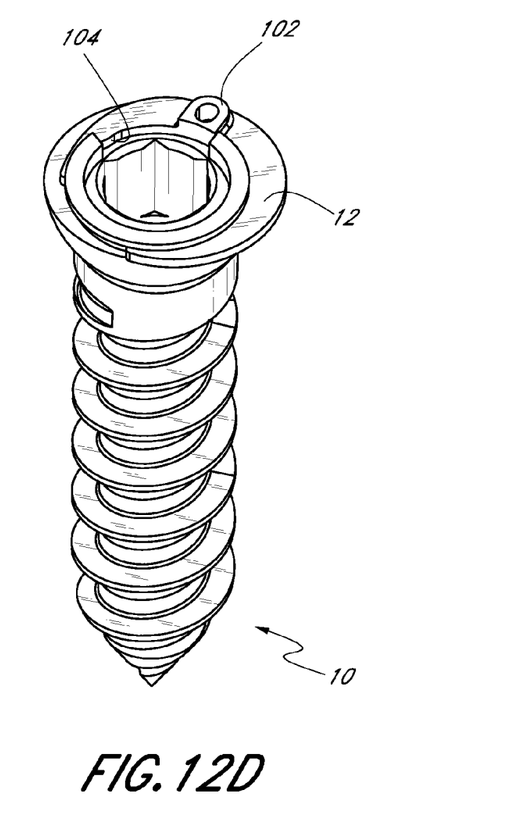
FIG. 12D is a perspective view of the screw and the locking ring illustrated in FIG. 12B in a locked position.

FIGS. 10 and 11 illustrate additional embodiments of a locking ring 12 and a screw 10, respectively. The locking ring 12 can include an anterior surface 46 and a posterior surface 48 (similar to that shown in FIG. 6). In certain embodiments, the locking ring 12 has a first protrusion 102 on the anterior surface 46 and/or the inner curved surface 44 of the locking ring 12. The first protrusion 102 can have a means to assist in rotation of the locking ring 12 (e.g. a hole 40, etc.). At least a portion of the upper portion 26 and/or the groove 28 of the head 24 can have a first notch 114 to form a c-shape. The first protrusion 102 can reside and/or be within the first notch 114 when the ring 12 is in the groove 28. As illustrated in FIGS. 12A-D, the first protrusion 102 can restrict the rotational movement of the locking ring 12. When the first protrusion 102 is at one end of the first notch 114, the locking ring 12 can be in an unlocked position, as illustrated in FIGS. 12A and 12C. When the first protrusion 102 is at the other end of the first notch 114, the locking ring 12 can be in a locked position, as illustrated in FIGS. 12B and 12D, extending outwardly beyond the lower portion 30 of the head 24.

In certain embodiments, the locking ring 12 has a second protrusion 104 on the inner curved surface 44. At least a portion of the groove 28 of the head 24 can have a second notch 112 (see FIG. 11). In an unlocked position, the second protrusion 104 is at least partially within the second notch 112. When the second protrusion 104 is at least partially within the second notch 112, the locking ring 12 is at least partially restricted from rotating out of the unlocked position. In certain embodiments, the torque required to rotate the locking ring 12 when the second protrusion 104 is at least partially within the second notch 112 is greater than the torque required to rotate the locking ring 12 when the second protrusion 104 is not within the second notch 112. Advantageously, the rotational restriction of the locking ring 12 due to the second protrusion 104 being at least partially within the second notch 112 at least partially limits the locking ring 12 from rotating during insertion of the screw 10 into the plate 14. However, in certain embodiments, the rotational restriction of the locking ring 12 due to the second protrusion 104 being at least partially within the second notch 112 is less than the rotational force that a tool can exert so that the locking ring 12 can be rotated with the tool. In certain embodiments, the locking ring 12 has a second protrusion 104 while the groove 28 of the head 24 does not have a second notch 112.

In a locked position, the second protrusion 104 is at least partially within the first notch 114 and outside the second notch 112, as illustrated in FIGS. 12B and 12D. The second protrusion 104 at least partially restricts the locking ring 12 from rotating into an unlocked position. In certain embodiments, the second protrusion 104 is at one end of the first notch 114 and the first protrusion 102 is at the other end of the first notch 114. Advantageously, when the second protrusion 104 and the first protrusion 102 are at opposite ends of the first notch 114, the locking ring 12 is at least partially restricted from rotating in either direction. In certain embodiments, the rotational restriction of the locking ring 12 due to the second protrusion 104 at least partially within the first notch 114 is less than that required to rotate the locking ring 12 with a tool. Advantageously, by being able to unlock the locking ring 12 after the locking ring 12 has been placed into a locked position, the screw 10 is able to be removed after the screw 10 and plate 14 have been installed. In certain embodiments, the second protrusion 104 can be on the posterior surface 46 and/or the anterior surface 48 of the locking ring 12, and the second notch 112 can be on the upper portion 26 and/or the lower portion 30 of the head 24, respectively. In further embodiments, the groove 28 includes the second protrusion 104 and the locking ring 12 includes the second notch 112. In some embodiments, the second protrusion 104 is within the second notch 112 when in a locked position. While some preferred configurations have been described in detail above, other configurations for releasably holding the locking ring in unlocked and/or locked positions are possible and can be used.

Figure 13:
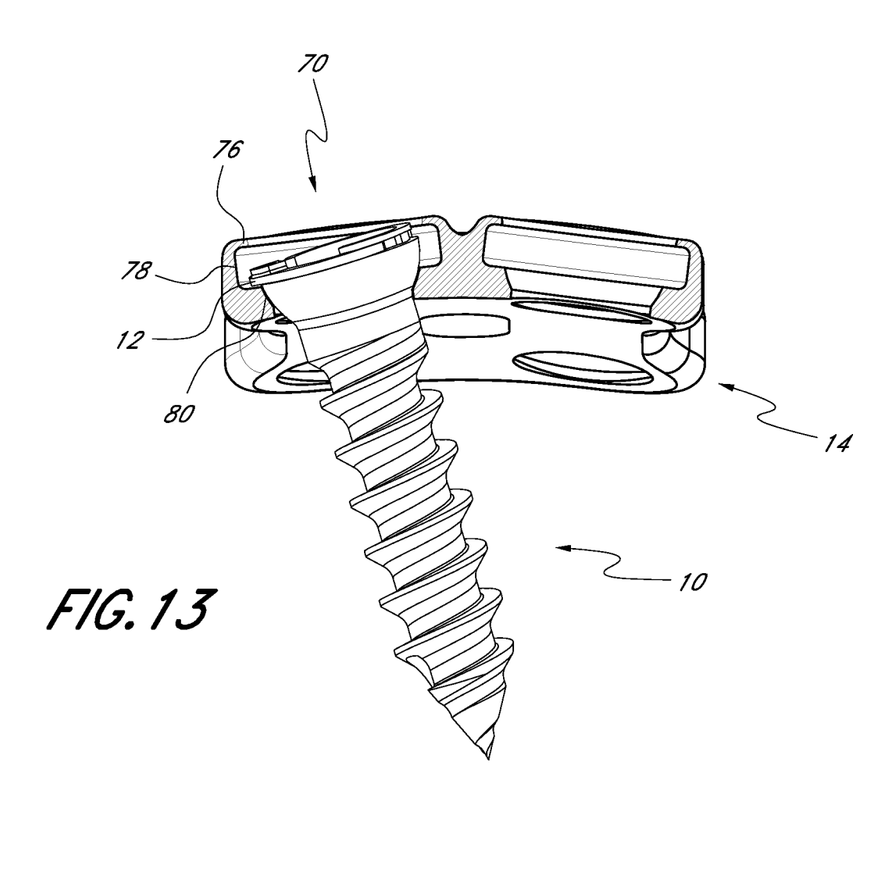
FIG. 13 is a cross-sectional view of an embodiment of a bone plate system illustrating that certain embodiments of bone plate systems are able to have the screw positioned at different angles relative to the plate.

In certain embodiments, the screw 10 can be at an angle within the through-hole 70 of the plate 14, as illustrated in FIG. 13. For example, the screw 10 can be screwed into a vertebral body at an angle non-perpendicular to the plate 14. Advantageously, this allows more options of placement of screws 10 in the vertebrae. In certain embodiments, a thickness of the groove 78 of the through-hole 70 is large enough that when the locking ring 12 is rotated into a locked position, the locking ring 12 can at least partially be within the groove 78. The locking ring 12 in FIG. 13 is illustrated in a locked position. When the screw 10 is at an angle, the locking ring 12 may also be at an angle. A larger thickness of the groove 78 preferably allows a locking ring 12 at an angle to at least partially reside within the groove 78. If the thickness of the groove 78 is not large enough to accommodate the locking ring 12 at a particular angle, the locking ring 12 may impinge on the upper portion 76 and/or the lower portion 80 of the through-hole 70 and not be able to be rotated into a locked position.

Figure 14:
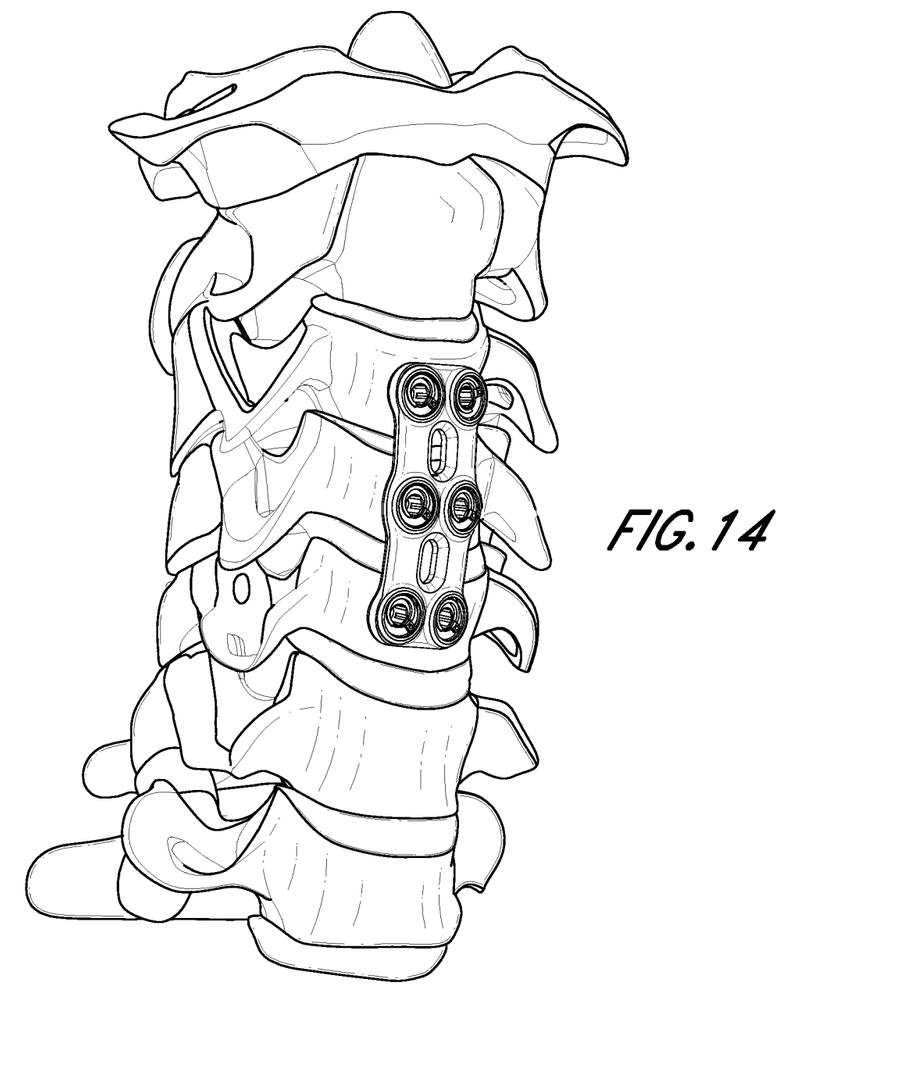
FIG. 14 is a perspective view of an embodiment of a bone plate system implanted in vertebrae of a patient.

The bone plate systems discussed above can be used to fix adjacent vertebrae. FIG. 14 shows one embodiment of a bone plate system implanted in vertebrae of a patient. For example, the plate 14 can be positioned on the anterior surface of at least two adjacent vertebral bodies. At least one through-hole 70 can be positioned over a first vertebral body and a second through-hole 70 can be positioned over a second vertebral body. A screw 10 can be inserted through one of the through-holes 70 into the first vertebral body and a second screw 10 can be inserted through another through-hole 70 into the second vertebral body. The threaded body of the screws 10 can engage with the vertebral bodies. A locking ring 12 can be positioned into a locking position. For example, the locking ring can be rotated so that the locking ring 12 is within the groove 28 of the head 24 of at least one of the screws 10, and the locking ring 12 is positioned at least partially within a groove 78 of one of the through-holes 70 to limit the screw 10 backing out of the through-hole 70.

A number of surgical methods can be used to implant bone plate systems. For example, several surgical methods are described in U.S. Pat. No. 7,674,279, herein incorporated by reference in its entirety. For example, the patient can be placed on the operating room table in the supine position with the head in slight extension and slight rotation opposite the side of incision.

After decompression and interbody grafting procedures have been completed, anterior osteophytes can be removed to provide a contoured contact surface for positioning the plate 14. The plate 14 can be selected so that the edges do not extend over adjacent disc spaces. The plate 14 can be pre-contoured with lordotic curvature to minimize the amount of intra-operative contouring required. A plate bender can also used for contouring.

The plate 14 can then be positioned over vertebral bodies using a plate holder, and then the plate 14 can be confirmed that it is properly aligned in mediolateral and caudocranial position. The position of the plate 14 can be temporary fixed using pins (e.g., temporary pins, etc.). The pins can be inserted with a tool (e.g., screwdriver, etc.). The pins can be inserted through any of the screw holes and can provide stability during placement of the screw 10.

An awl may be used to create a pilot hole before inserting the screw 10. The awl is placed in one of the through-holes 70 of the plate 14. In certain embodiments, the awl is placed at an angle of up to about 14° from a perpendicular axis to the plate 14. The awl is pressed and rotated in the bone until a depth has been reached. For example, the awl can be inserted until it has bottomed out. In certain embodiments, the awl can provide a depth of about 10 mm. Alternatively, a drill guide and drill can be used to create a pilot hole. The drill guide can be attached to the plate 14 and the drill can create a pilot hole. In certain embodiments, the drills are about 12, 14, or 16 mm in length. The screws 10 can be self-tapping and/or self-drilling screws so that tapping may not be used. In some cases, where the bone is hard cortical bone, tapping may still be used. In certain embodiments, the tap is provided at a depth of about 10 mm. In certain embodiments, the self-tapping or self-drilling screws have a length of about 12, 14, 16, or 18 mm with a diameter of about 4.0 mm. An about 4.5 mm diameter screw can also be used if there is additional bone purchase. The above screw lengths are measure from under the head 24 of the screw 10 to the end of the distal end 20 of the screw 10. In certain embodiments, the screws are inserted using a hex screwdriver.

The plate 14 may vary in size. For example, the length and level number of the plate 14 may vary. The level number of the plate 14 indicates the number of vertebral body connections made by plate 14. In some embodiments, a 1-level plate 14 preferably has a length from about 20 mm to about 32 mm and connects two vertebral bodies. In some embodiments, a 2-level plate 14 preferably has a length from about 37 mm to about 55 mm and connects three vertebral bodies. In some embodiments, a 3-level plate 14 preferably has a length from about 54 mm to about 75 mm and connects four vertebral bodies. In some embodiments, a 4-level plate 14 preferably has a length from about 69 mm to about 89 mm and connects five vertebral bodies.

The screw 10 can be inserted into vertebrae until it rests firmly inside the through-hole 70 of the plate 14. Once the screws 10 have been seated, positioned and tightened, then locking ring 12 can be rotated to a locked position. If desired, the screws 10 can be subsequently removed by rotating the locking ring 12 to an unlocked position and removing the screws 10. In certain embodiments, the screws 10 can be repositioned, tightened and then locked again without mechanically weakening the locking mechanism. Visual and radiographic confirmation of plate, screw and bone graft placement can be done, and the incision can then be closed.

The various screws and methods described above provide a number of ways to carry out some preferred embodiments of the invention. Of course, it is to be understood that not necessarily all objectives or advantages described may be achieved in accordance with any particular embodiment described herein. Thus, for example, those skilled in the art will recognize that the devices and systems may be made and the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various components, features and steps discussed above, as well as other known equivalents for each such component, feature or step, can be mixed and matched by one of ordinary skill in this art to make devices and systems and perform methods in accordance with principles described herein.

Although the invention has been disclosed in the context of some embodiments and examples, it will be understood by those skilled in the art that the invention extends beyond these specifically disclosed embodiments to other alternative embodiments and/or uses and obvious modifications and equivalents thereof. Accordingly, the invention is not intended to be limited by the specific disclosures of preferred embodiments herein.

What is claimed is:

1. A bone plate locking system comprising:
    a threaded screw body having a proximal end and a distal end, the proximal end comprising a head, the head comprising an upper portion, a groove adjacent the upper portion defining an at least partially circular surface, a lower portion adjacent the groove, a notch in at least a portion of the groove and a notch in at least a portion of the upper portion, a center-axis of the threaded screw body passing through both the proximal end and distal end of the threaded screw body, a center-axis of the groove of the head substantially parallel to the center-axis of the threaded screw body, wherein the center-axis of the groove of the head is off-axis to the center-axis of the threaded screw body, and wherein the lower portion of the head is centered on the center-axis of the threaded screw body;
    a locking ring configured to at least partially reside within the groove of the head, the locking ring comprising an outer curved surface, an inner curved surface, an anterior surface, a posterior surface, a first protrusion on at least a portion of the anterior surface of the locking ring that is configured to reside within the notch in the upper portion of the head and a second protrusion on at least a portion of the inner curved surface; and
    a plate comprising an anterior surface, a posterior surface and at least one through-hole through the anterior surface and the posterior surface, the through-hole comprising an upper portion, a groove adjacent the upper portion and a lower portion adjacent the groove, the head of the screw body being receivable in the through-hole;
    wherein the locking ring is adapted to be rotatably positioned around the groove of the head such that in an unlocked position the locking ring is outside the groove of the through-hole, the first protrusion is at one end of the notch in the upper portion of the head and the second protrusion of the locking ring is within the notch in the groove of the head, and in a locked position the locking ring is at least partially within the groove of the through-hole, the first protrusion is at another end of the notch in the upper portion of the head and the second protrusion of the locking ring is outside the notch in the groove of the head.

2. A bone plate locking system comprising:
    a threaded screw body having a proximal end and a distal end, the proximal end comprising a head, the head comprising an upper portion, a groove adjacent the upper portion and a lower portion adjacent the groove, a center-axis of the threaded screw body passing through both the proximal end and distal end of the threaded screw body, a center-axis of the groove of the head substantially parallel to the center-axis of the threaded screw body, wherein the center-axis of the groove of the head is off-axis to the center-axis of the threaded screw body, and wherein the lower portion of the head is centered on the center-axis of the threaded screw body;
    a locking ring configured to at least partially reside within the groove of the head; and
    a plate comprising an anterior surface, a posterior surface and a through-hole through the anterior surface and the posterior surface, the through-hole comprising an upper portion, a groove adjacent the upper portion and a lower portion adjacent the groove, the head is receivable in the through-hole;
    wherein the locking ring is adapted to be rotatably positioned around the groove of the head such that in an unlocked position the locking ring is outside the groove of the through-hole and in a locked position the locking ring is at least partially within the groove of the through-hole.

3. The bone plate locking system of claim 2, wherein the locking ring comprises a hole to rotate the locking ring.

4. The bone plate locking system of claim 2, wherein the locking ring has a c-shape.

5. The bone plate locking system of claim 2, wherein the locking ring comprises an outer curved surface and an inner curved surface, at least a portion of the locking ring has a distance between the outer curved surface and the inner curved surface that is greater than at least another portion of the locking ring.

6. The bone plate locking system of claim 2, further comprising more than one threaded screw body and more than one locking ring, wherein the plate comprises more than one through-hole.

7. The bone plate locking system of claim 2, wherein in the locked position, the locking ring substantially limits the screw from backing out of the plate.

8. The bone plate locking system of claim 2, wherein the locking ring is able to be in a locked position when the screw is non-perpendicular to plate.

9. The bone plate locking system of claim 2, wherein the head of the threaded screw body further comprises a first notch in at least a portion of the upper portion of the head, the locking ring further comprises an anterior surface, a posterior surface, and a first protrusion on at least a portion of the anterior surface that is configured to reside within the first notch in the upper portion of the head, and the first protrusion is at one end of the first notch in the upper portion of the head in the unlocked position and the first protrusion is at another end of the first notch in the upper portion of the head in the locked position.

10. The bone plate locking system of claim 9, wherein the head of the threaded screw body further comprises a second notch in at least a portion of the groove of the head, the locking ring further comprises an inner surface and a second protrusion on at least a portion of the inner surface, and the second protrusion of the locking ring is within the second notch in the groove of the head in the unlocked position and the second protrusion is outside the second notch in the groove of the head in the locked position.

11. The bone plate locking system of claim 2, wherein the head of the threaded screw body further comprises a notch in at least a portion of the groove of the head, the locking ring further comprises an inner surface and a protrusion on at least a portion of the inner surface, the protrusion of the locking ring is within the notch in the groove of the head in the unlocked position and the protrusion is outside the notch in the groove of the head in the locked position, and the upper portion of the head and the groove of the head are located proximal the lower portion of the head.

12. A method of fixing adjacent vertebrae, comprising:
providing a plate comprising an anterior surface, a posterior surface and a plurality of through-holes through the anterior surface and the posterior surface; the through-holes comprising an upper portion, a groove adjacent the upper portion and a lower portion adjacent the groove;
positioning the plate on the anterior surface of at least two adjacent vertebral bodies, wherein at least one through-hole is positioned over a first vertebral body and a second through-hole is positioned over a second vertebral body;
inserting a first threaded screw body through a first through-hole into the first vertebral body and a second threaded screw body through a second through-hole into the second vertebral body, the first and second threaded screw bodies comprising a proximal end and a distal end, the proximal end comprising a head, the head comprising an upper portion, a groove adjacent the upper portion and a lower portion adjacent the groove, a center axis of the threaded screw body passing through both the proximal end and distal end of the threaded screw body, a center-axis of the groove of the head substantially parallel to the center-axis of the threaded screw body, wherein the center-axis of the groove of the head is off-axis to the center-axis of the threaded screw body, wherein the lower portion of the head is centered on the center-axis of the threaded screw body, the heads of the threaded screw bodies positioned within first and second through-holes and the threaded screw bodies engaging the vertebral bodies; and
rotating a locking ring positioned within a groove of the head of one of said threaded screw bodies from an unlocked position where the locking ring is outside a groove of one of the through-holes to a locked position where the locking ring is positioned at least partially within a groove of one of the through-holes to limit the screw backing out of the through-hole.

13. The method of claim 12, wherein one of the screws is non-perpendicular to plate.

14. The method of claim 12, wherein the locking ring comprises an outer curved surface and an inner curved surface, at least a portion of the locking ring has a distance between the outer curved surface and the inner curved surface that is greater than at least another portion of the locking ring.

15. The method of claim 12, further comprising rotating a locking ring positioned within a groove of the head of another one of said threaded screw bodies to a position where the locking ring is positioned at least partially within a groove of one of the through-holes to limit the threaded screw body backing out of the through-hole.

16. The method of claim 12, wherein the head of one of said threaded screw bodies comprises a first notch in at least a portion of the head, the locking ring comprises an posterior surface and a first protrusion on at least a portion of the posterior surface that is configured to reside within the first notch of the head; and further comprising moving the first protrusion from one end of the first notch to the other end of the first notch.

17. The method of claim 16, wherein the head of one of the threaded screw bodies comprises a second notch in at least a portion of the groove, the locking ring further comprises an inner surface and a second protrusion on at least a portion of the inner surface; and further comprising moving the second protrusion from being within the second notch to being outside the second notch.

18. The method of claim 12, wherein the head of the one of the threaded screw bodies further comprises a notch in at least a portion of the groove, the locking ring further comprises an inner surface and a protrusion on at least a portion of the inner surface;
and further comprising moving the protrusion from being within the notch to being outside the notch.

19. A bone plate locking system comprising:
a threaded screw body having a proximal end and a distal end, the proximal end comprising a head, the head comprising an upper portion, a groove adjacent the upper portion and a lower portion adjacent the groove, a center-axis of the threaded screw body passing through both the proximal end and distal end of the threaded screw body, a center-axis of the groove of the head substantially parallel to the center-axis of the threaded screw body, wherein the center-axis of the groove of the head is off-axis to the center-axis of the threaded screw body, and wherein the lower portion of the head is centered on the center-axis of the threaded screw body;
a locking ring configured to at least partially reside within the groove of the head; and
a plate comprising an anterior surface, a posterior surface and a through-hole through the anterior surface and the posterior surface, the through-hole comprising an upper portion, a groove adjacent the upper portion and a lower portion adjacent the groove, the head is receivable in the through-hole;
wherein rotation of the locking ring about the center-axis of the groove of the head in a first direction into a locked position displaces a portion of the locking ring within the groove of the through-hole and rotation of the locking ring about the center-axis of the groove of the head in a second direction into an unlocked position displaces a portion of the locking ring outside the groove of the through-hole.

20. The bone plate locking system of claim 19, wherein the groove of the head is circular in shape.

21. The bone plate locking system of claim 20, wherein the groove of the through-hole is circular in shape.

22. The bone plate locking system of claim 19, wherein the locking ring may be installed in the threaded screw body before installing the threaded screw body through the through-hole.

23. The bone plate locking system of claim 19, wherein the locking ring prevents the threaded screw body from backing out of the through-hole when the locking ring is in a locked position.

24. The bone plate locking system of claim 23, wherein the groove of the head comprises a notch.

25. The bone plate locking system of claim 23, wherein the through-hole further comprises a center axis;
wherein the groove of the through-hole is large enough to accommodate the locking ring in a locked position when the center axis of the threaded screw body is not substantially parallel to the center axis of the through-hole.

26. The bone plate locking system of claim 25, wherein the locking ring comprises an inner surface, an outer surface, a posterior surface, and an anterior surface;
wherein the anterior surface comprises a projection configured to interfere with the notch of the groove of the head and limit the rotation of the locking ring.

27. The bone plate locking system of claim 26, wherein the groove of the head comprises a second notch;
   wherein the inner surface of the locking ring comprises a second protrusion configured to slideably engage the second notch of the groove of the head to maintain either the locked or unlocked position of the locking ring and;
   wherein the upper portion of the head and the groove of the head are located proximal the lower portion of the head.

\* \* \* \* \*